US012741928B2

(12) United States Patent
Gopalan et al.

(10) Patent No.: US 12,741,928 B2
(45) Date of Patent: Sep. 22, 2026

(54) FORMAMIDE MONOMERS AND POLYMERS SYNTHESIZED THEREFROM

(71) Applicant: Wisconsin Alumni Research Foundation, Madison, WI (US)

(72) Inventors: Padma Gopalan, Madison, WI (US); Balamurugan Ayyakkalai, Madison, WI (US); Ri Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 795 days.

(21) Appl. No.: 18/149,345

(22) Filed: Jan. 3, 2023

(65) Prior Publication Data

US 2023/0159435 A1 May 25, 2023

Related U.S. Application Data

(62) Division of application No. 16/815,772, filed on Mar. 11, 2020, now Pat. No. 11,572,335.

(60) Provisional application No. 62/818,188, filed on Mar. 14, 2019.

(51) Int. Cl.

| | |
|---|---|
| ***C07C 225/16*** | (2006.01) |
| ***C07C 225/14*** | (2006.01) |
| ***C08F 12/26*** | (2006.01) |

(52) U.S. Cl.

CPC .......... *C07C 225/16* (2013.01); *C07C 225/14* (2013.01); *C08F 12/26* (2013.01); *C07C 2602/42* (2017.05)

(58) Field of Classification Search

CPC ...... C07C 225/16; C07C 225/14; C08F 12/26

See application file for complete search history.

(56) References Cited

FOREIGN PATENT DOCUMENTS

| | | | |
|---|---|---|---|
| GB | 1064835 | A | 4/1967 |
| JP | 2001310567 | A | 11/2001 |

OTHER PUBLICATIONS

Neochoritis, C.G. et al. "Efficient Isocyanide-less Isocyanide-Based Multicomponent Reactions" (Org. Lett. 2015, 17, 2002-2005) ( Year: 2015).*

Neochoritis, C.G. et al. "Efficient Isocyanide-less Isocyanide-Based Multicomponent Reactions" Supplementary Information (Org. Lett. 2015, 17, S1-S148) (Year: 2015).*

Kreye, O. et al. "Multicomponent Reactions with a Convertible Isocyanide: Efficient and Versatile Grafting of ADMET-Derived Polymers" (Macromol. Chem. Phys. 2014, 215, 2207-2220) (Year: 2014).*

Oelmann, S. et al. "Controlling molecular weight and polymer architecture during the Passerini three component step-growth polymerization" (Polym. Chem., 2016, 7, 1857-1860) (Year: 2016).*

Corain, Benedetto, Marino Basato, Marco Zecca, Silvano Lora, and Giancarlo Palma. "Radiation-induced synthesis of novel isonitrile functionalized polymers." Die Makromolekulare Chemie, Rapid Communications 7, No. 10 (1986): 651-653.

European Search Report, Nov. 29, 2022, European Patent Office, Munich, Germany.

Chinese First Office Action, Nov. 1, 2023, China National Intellectual Property Administration.

* cited by examiner

*Primary Examiner* — Andrew S Rosenthal

(74) *Attorney, Agent, or Firm* — Bell & Manning, LLC

(57) ABSTRACT

Formamide group-containing monomers and polymers made by polymerizing the monomers are provided. Also provided are methods of polymerizing the monomers and methods of synthesizing functionalized polymers by pre- and/or post-polymerization functionalization. The monomers are non-toxic and can generate highly reactive isocyanate and isonitrile precursors in a one-pot synthesis that enables the incorporation of complex functionalities into the side-chain of the polymers that are synthesized from the monomers.

28 Claims, 14 Drawing Sheets

R1=Me, Et, Bn, tBu, iPr, Cl, Br
Formamide
PhI(OCOCF3)2
DCE, 60 °C, 1 h
4 A°MS, N2
Isocyanate
R2OH
R2R3NH
H2O
Urethane
Urea
Passerini 3-CR
R2-CHO
R3-COOH
α-acyloxycarboxmide
Ugi-beta-lactum-3CR
β-lactum derevative
Ugi-tetrazole variation-4CR
Tetrazole derevative
Ugi-4CR
R2-CHO
R3-COOH
R4-NH2
α-acylamlnocarboxmide 0.92
1.10
4.13
2.00
8.5
8.0
7.5
7.0
6.5
6.0
5.5
5.0
4.5
4.0 a
e
b+b'
c+c'+f
d
HN
H
O
x
1.00
1.20
5.89
2.19
9.0
8.5
8.0
7.5
7.0
6.5
6.0
5.5
5.0
4.5

R = H or R = Me

HCOOEt

COCl

TEA

NHCO $N_2$

DCC

DMAP

TEA

POCl$_3$
TEA
12hr
1
2
DCM
ATRP
initiator
Styrene monomer
NMP
initiator
4
RAFT
polymerization
5
1) ATRP M$_1$
2) NMP M$_2$
Bottle-brush copolymer
with 1:1 ratio of
polymer A:B
ROMP
1) ATRP M$_1$
2) NMP M$_2$

FIG. 11

FORMAMIDE MONOMERS AND POLYMERS SYNTHESIZED THEREFROM

CROSS-REFERENCE TO RELATED APPLICATIONS

The present application is a divisional of U.S. patent application Ser. No. 16/815,772, that was filed Mar. 11, 2020, which claims priority to U.S. provisional patent application No. 62/818,188 that was filed Mar. 14, 2019, the entire contents of which are incorporated herein by reference.

REFERENCE TO GOVERNMENT RIGHTS

This invention was made with government support under DMR1121288 awarded by the National Science Foundation. The government has certain rights in the invention.

BACKGROUND

Recent advances in controlled polymerization methods allow unprecedented access to polymers with well controlled architectures, molecular weights, and dispersities. Advances in living or controlled free radical polymerization (LFRP) and ring opening metathesis polymerization (ROMP) and the development of associated initiators and catalysts have rapidly expanded the diversity of polymers and their properties. These methods have resulted in new types of block copolymers (BCPs), bottle-brush copolymers, polymer brushes, polymer stars, and other complex architectures. However, their further utility requires incorporation of multi-functional groups, which is challenging.

The list of chemical transformations used to modify polymer side groups is quite large. Though these transformations might be very efficient for small molecules, implementing them on polymer chains with high efficiencies and yields, and in a scalable manner, while accessing a rich range of orthogonal functionalities, using relatively mild conditions, is still a challenge. Isocyanate and isonitrile functionalities are commonly used to form urea, urethane, thiourea, acyloxycarboxamide, lactam's, and tetrazole linkages, to name a few. However, the safety issues presented by these chemicals have not been addressed extensively. The handling, manufacturing, and transport of these isocyanate and isonitrile chemicals are highly dangerous due to their toxicity. Hence, in spite of the incredible advances made in the development of new polymer functionalization routes, there is a continued need for newer, more efficient methodologies.

SUMMARY

Formamide group-containing monomers and polymers made by polymerizing the monomers are provided. Also provided are methods of polymerizing the monomers and methods of functionalizing polymers made from the monomers.

One embodiment of a formamide group-containing monomer includes a formamide functionality attached to a polymerizable group, wherein the polymerizable group comprises a styrene group, an acrylate group, a methacrylate group, or a cyclic olefin group. Various polymers can be formed by polymerizing one or more of the formamide group-containing monomers and, optionally, one or more additional monomers.

The formamide functionalities can be converted into reactive isocyanate functionalities and/or isonitrile functionalities, either before or after the monomers are polymerized. The isocyanate and isonitrile groups can then be converted into a variety of chemically useful functional groups. Such functional groups include urethane groups, urea groups, carboxamide groups, β-lactam derivatives, tetrazole derivatives, ATRP initiating groups, and NMP initiating groups.

In some embodiments in which formamide groups are converted into isocyanate groups, the conversion of the formamide groups and the transformation of the isocyanate groups are carried out in a multicomponent reaction.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 7D depicts a synthetic scheme for (meth)acrylate formamide monomers. FIG. 7E-FIG. 7G depict synthetic schemes for three cyclic olefin monomers, in this case, norbornene formamide (NBF) monomers. FIG. 7H shows norbornene derivatives that can be used in the synthesis of a ROMP monomer.

FIG. 11 depicts a summary of proposed homo and random copolymers. The VBF (upper left scheme), (M)AF (lower left scheme), and VBF (upper and lower right schemes) are copolymerized with methyl methacrylate (MMA), methacrylate (MA), and norbornene (NB), respectively. The ratio of x:y will be varied from 7:3, 1:1, to 2:8.

DETAILED DESCRIPTION

Figure 1:
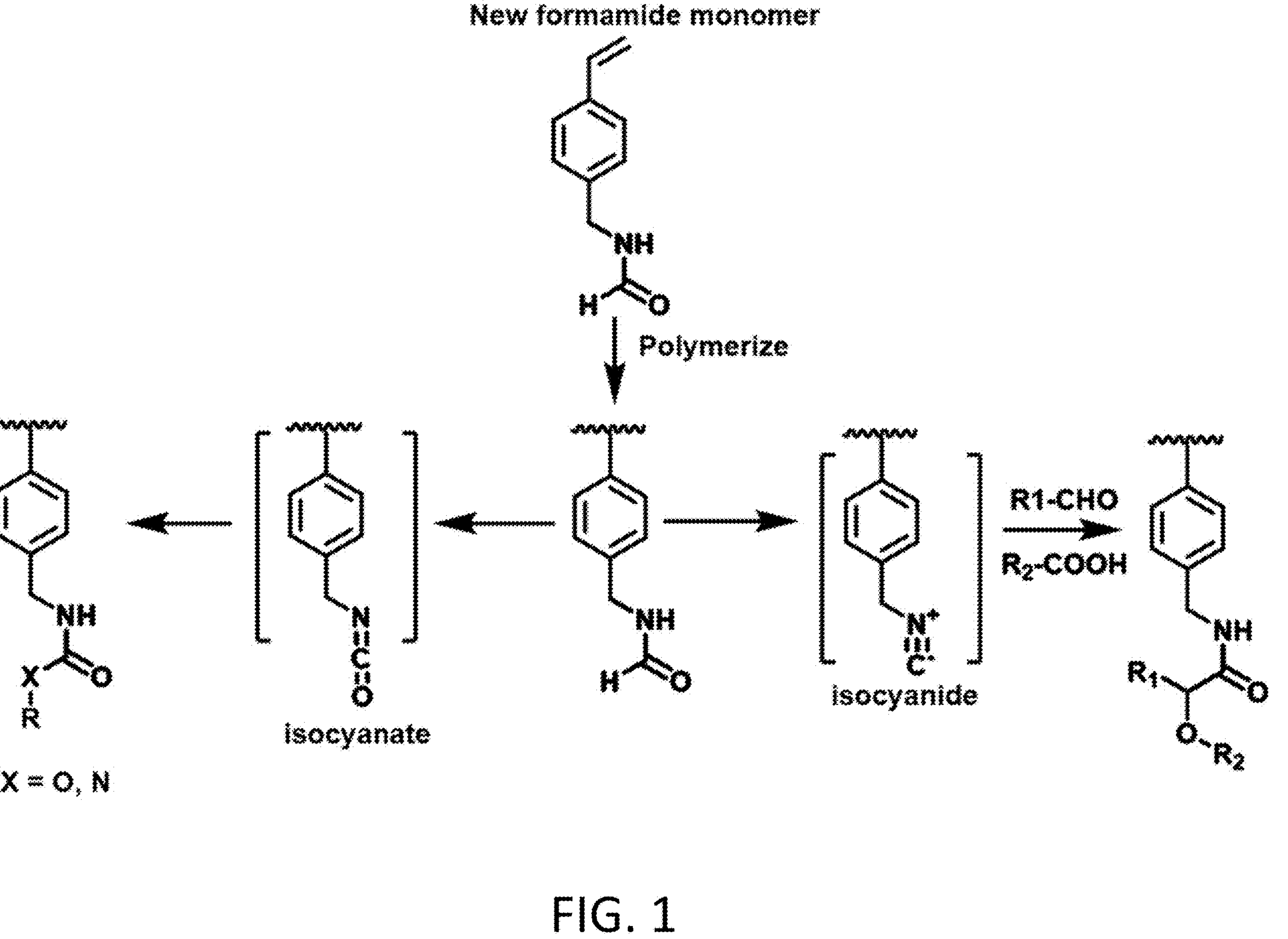
FIG. 1 depicts the structure of a formamide monomer and its polymerization, followed by its transformation to isocyanate and isocyanide intermediates and subsequent functionalization to urea, urethane, and acyloxycarboxamide and acylaminocarboxamide derivatives using one-pot multicomponent reactions (MCR).

Formamide group-containing monomers (also referred to herein as formamide monomers) and polymers made by polymerizing the monomers are provided. Also provided are methods of polymerizing the monomers and methods of synthesizing functionalized polymers by pre- and/or post-polymerization functionalization.

The monomers are non-toxic and can generate highly reactive isocyanate and isonitrile precursors in a one-pot synthesis that enables the incorporation of complex functionalities into the side-chain of the polymers that are synthesized from the monomers. As such, the monomers and the polymers formed therefrom vastly expand isonitrile/isocyanate-based reactive chemistry to impart complex functional groups to polymers without the need to handle, use, or transport toxic isocyanate or isonitrile monomers. The resulting polymers have uses in biomedical, pharmaceutical, electronics, and coatings applications and as reactive polymer supports. For example, polymers with reactive functional groups can be used for the immobilization of industrially relevant enzymes on polymeric substrates to conduct large scale enzymatic reactions, as templates to facilitate organic transformations, as reactive resins, and as surfaces for cell growth and expansion.

The formamide monomers include one or more formamide functionalities (—NH—C═O) attached to a polymerizable group. Examples of polymerizable groups include vinyl groups, styrene groups, acrylate groups, methacrylate groups, and cyclic olefin groups.

Polymerizable styrene groups polymerize via their vinyl double bonds to form a polymer backbone containing a carbon-carbon chain. The formamide functionalities can be located at the para, ortho, or meta positions on the benzene ring of the styrene group. The styrene groups include styrene derivative groups, such as t-butyl styrene groups, that include another functional group, in addition to the formamide group(s), pendant from their benzene ring. Various styrene derivative groups can be synthesized by the Friedel-Craft reaction.

Acrylate and methacrylate groups (collectively referred to as (meth)acrylate groups) polymerize via their vinyl group and R—C═C($CH_3$)H double bond, respectively, to form a polymer backbone containing a carbon-carbon chain.

Cyclic olefins polymerize via an aromatic carbon-carbon double bond via ROMP to form a polymer backbone chain that includes carbon-carbon double bonds. Depending upon the cyclic olefin group being used, the polymer backbone chain may also include cyclic rings. Examples of cyclic olefin groups include norbornene groups. The norbornene groups include norbornene derivative groups that include another functional group, in addition to the formamide group(s), pendant from their norbornene rings.

The formamide functionalities are attached to the polymerizable groups via a linker. In some of the formamide monomers, the linker is a single carbon atom. However, the length of the linker can be selected to provide for desired properties, such as enhanced solubility in a given organic solvent. By way of illustration, the linker can contain a carbon chain of two or six carbon atoms, although longer carbon chains can also be employed. However, the linker need not consist only of carbon atoms. Other groups, including ether linkages, ester linkages, and/or aryl groups can be part of the linker.

Figure 6:
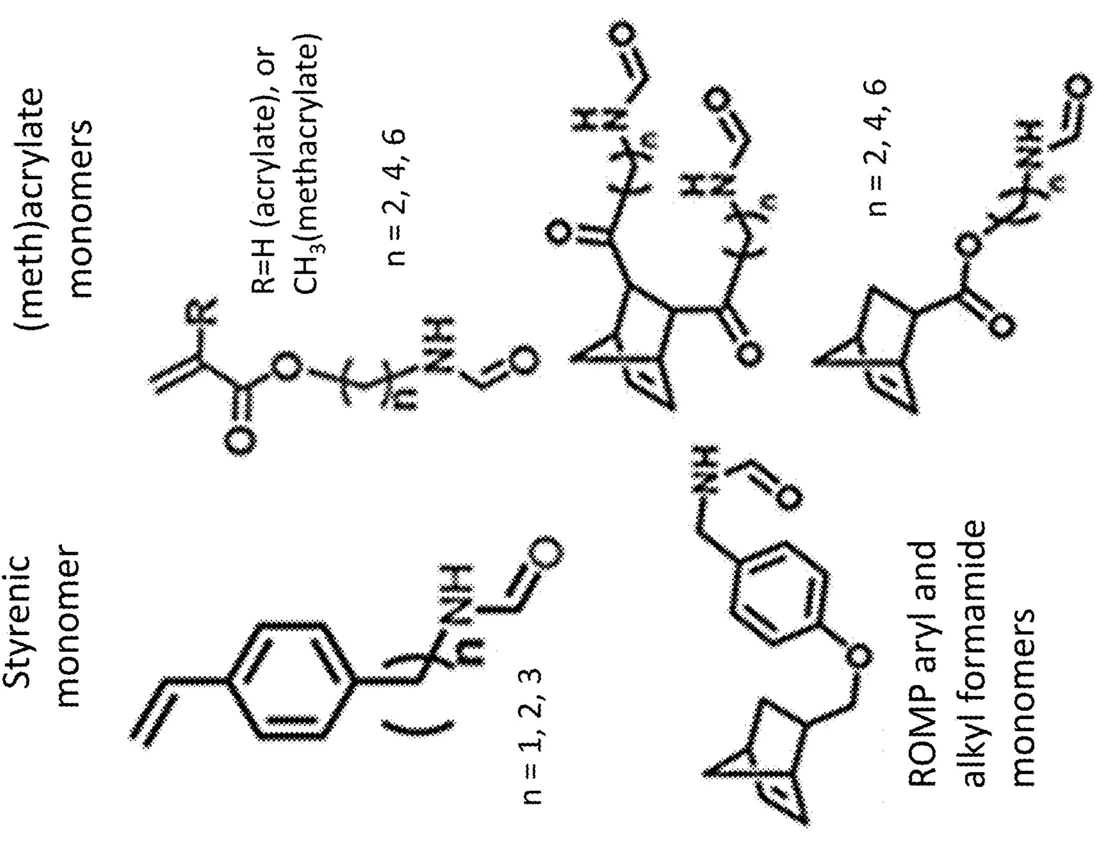
FIG. 6 depicts the structure of styrenic, (meth)acrylate ((M)AF), and cyclic olefin formamide monomers.

Examples of formamide monomers are shown in FIG. 6. These include: a styrenic formamide monomer that includes a formamide functionality attached to a styrene group via a carbon linker that can contain 1, 2, or 3 carbon atoms (top left panel); a (meth)acrylate formamide monomer that includes a formamide functionality attached to a (meth) acrylate group via a carbon chain linker that contains from two to six carbon atoms (top right panel); a cyclic olefin formamide monomer that includes a formamide functionality attached to a norbornene group via a linker comprising an ether linkage and an aryl group (bottom left panel); a cyclic olefin formamide monomer that includes two formamide functionalities, each attached to a norbornene group via a linker comprising a carbonyl group and a carbon chain having from two to six carbon atoms (bottom right panel); and a cyclic olefin formamide monomer that includes a formamide functionality attached to a norbornene group via a linker comprising an ester linkage and a carbon chain having from two to six carbon atoms (bottom right panel).

A detailed description of methods of synthesizing formamide monomers is provided in Example 2. Generally, the formamide monomers can be made by reacting a formamide precursor with a monomer that includes the polymerizable group. The formamide precursor can be a chemical that includes a formamide group or a chemical that forms the formamide functionality upon reaction with the monomer having the polymerizable group.

The formamide monomers can be polymerized to form homopolymers or copolymerized with one or more additional monomers to form copolymers. The additional monomers can include other formamide monomers, non-formamide monomers, or a combination thereof. The copolymers may be random copolymers or block copolymers. Examples of other monomers with which the formamide monomers can be polymerized include vinyl monomers, styrene monomers, styrene derivative monomers, such as t-butyl styrene monomers, acylate monomers, methacrylate monomers, epoxy group-containing monomers, such as glycidyl methacrylate monomers, vinyl pyridine monomers, 4,4-dimethyl-2-vinylazlactone monomers, and cyclic olefin monomers. The mole ratios of the various monomers in the polymers can be tailored to provide desired polymer properties and solubilities. Therefore, the amount of formamide monomer in a polymer will depend on the intended application for the polymer. By way of illustration, in various embodiments of the copolymers polymerized from the formamide monomers, the formamide monomers will account for at least 0.1 mol. %, at least 1 mol. %, at least 5 mol. %, at least 10 mol. %, at least 25 mol. %, at least 50 mol. %, at least 75 mol. %, at least 90 mol. %, at least 95 mol. %, at least 99 mol. %, and at least 99.9 mol. % of the copolymer. The monomers can be polymerized using known polymerization techniques for vinyl, (meth)acrylate, and cyclic olefin monomers, as illustrated in the Examples. These include free radical polymerization, RAFT polymerization, ATRP, and ROMP.

RAFT is a form of living radical polymerization that enables the polymerization of polymers with complex architectures, including block, graft, comb, and star structures. The RAFT process involves conventional free radical polymerization of a substituted monomer in the presence of a suitable chain transfer agent.

ATRP can be used to polymerize a wide variety of monomers with a high degree of control. Control in ATRP comes from the reversible redox activation of a dormant polymer chain-end (halide functionalized) by a halogen transfer to a transition metal complex.

ROMP is a form of living polymerization that is characterized by ease of polymerization, tolerance to functionality, and the ability to build complex structures from bi- and oligo-cyclic olefins. ROMP employs catalysts that generate a metallic carbene species that initiates polymerization of a cyclic olefin, resulting in a polymer with double bonds in the backbone. This feature allows the construction of complex, densely substituted structures.

The formamide functionality of the monomers or the polymers formed therefrom can be converted into a reactive isocyanate or a reactive isonitrile intermediate using known formamide reaction chemistries, and these reactive intermediates can then be converted into a wide range of useful functionalities. For example, formamide functionalities can be converted into isocyanate functionalities by reaction with an oxidant or converted into isonitrile functionalities by dehydration with a dehydrating agent. The conversion of the formamide functionalities into isocyanate or isonitrile groups can be carried out prior to or after formamide monomer polymerization. However, the pre-polymerization conversion generally requires the intermediates to be isolated prior to further functionalization, which can be a draw-back, since the intermediates are toxic. In contrast, the post-polymerization conversion of the formamide groups into isocyanate or isonitrile groups makes it possible to conduct further functionalization of the polymer in a multicomponent reaction (MCR; also referred to as a one-pot synthesis) without the need to isolate the toxic intermediates. Transformation reactions for isocyanates and isonitriles are well known, and these chemistries can be used in the one-pot syntheses. The MCRs based on these intermediates can involve two, three, four, or even more components in the reaction, opening up the ability to functionalize the polymers with a wide variety of complex orthogonal functional groups.

Isocyanate groups are a class of highly reactive functionalities for which are known a number of organic transformations, including reaction with diols to form polyurethanes. The formation of the urethane or carbamate link is ubiquitous in polymer post-functionalization reactions as well. Isonitriles are also an important class of reactive functionalities. Their reactivity comes from the carbon center that is divalent and hence can react with electrophiles and nucleophiles. They have been used in multicomponent reactions to form highly functional molecules. They are incorporated as one of the 3 components (3-CR) in a Passerini or 4-component (4-CR) Ugi reaction.

The conversion of the formamide groups into different functionalities via an isocyanate intermediate is illustrated using the simple case of a carbamate transformation in FIG. 1. In a first step, the formamide monomers are polymerized into a formamide-functionalized polymer. As shown in the reaction scheme proceeding to the left, in the presence of an oxidant, the formamide groups can be converted into intermediate isocyanate groups, which are then transformed by reaction with an alcohol into carbamate functionalities in a one-pot synthesis. This transformation is discussed in more detail in Example 1. Alternatively, the isocyanates can be converted into carbamide groups by reaction with a primary amine. By using oligomeric primary amines, the isocyanate groups can be converted into urea groups.

A more complex conversion is shown proceeding to the right in FIG. 1. Here, the formamide groups are first converted into isonitrile (also referred to as isocyanide) intermediates, which are transformed into acyloxycarboxamide functionalities by reaction with an aldehyde and an acid using a Passerini-3CR reaction in a one-pot synthesis. Other isonitrile conversions that can be used include conversion to a β-lactam group by reaction with an aldehyde and an amino acid using the Ugi-β-lactam-3CR reaction, the conversion to an acylaminocarboxamide by reaction with an aldehyde, an acid, and primary amine using a Ugi-4-CR reaction, and conversion to a tetrazole derivative by reaction with an aldehyde, a primary amine, and ammonia using a Ugi tetrazole reaction. These reactions are discussed in more detail in Example 3

The conversion of the formamide functionalities can lead to side-groups with complex branching structures, including bottle brush structures. By way of illustration, formamide groups can be converted into isonitrile groups, which can in-turn be transformed into branched side chains that include both an ATRP initiator and an NMP initiator. NMP is a controlled free-radical polymerization, in which polymerization is thermally initiated in the absence of an external radical source or a metal catalyst. In NMP, an alkoxyamine initiator can act as a unimolecular agent, providing both a reactive initiating radical and a stable mediating nitroxide radical. The ATRP initiators comprise alkyl halide groups, including secondary and tertiary alkyl halides. The two different initiators can then be reacted with two different monomers to grow to two different polymer chains from the main brush backbone. This chemistry is discussed in detail in Example 3.

The polymerization reactions and side group functionalizations can be conducted in a variety of organic solvents. The particular solvent used for a given polymerization/functionalization reaction will depend on the monomers and reactants being used. For example, for functionalization via an isocyanate intermediate, a wide range of solvents can be used, including mesitylene, diglyme, m-xylene, dimethylformamide (DMF), dimethyl sulfoxide (DMSO), acetonitrile (MeCN), and chlorinated solvents. Under oxidative conditions for the conversion of formamides to carbamates, a chlorinated solvent can be used. For functionalization via an isonitrile intermediate, the solvent used will depend on the dehydrating agent. For a conversion using triphosgene, a chlorinated solvent can be used.

EXAMPLES

The following examples illustrate the design and synthesis of formamide-based monomers that have been or can be polymerized. The formamide side-groups of the monomers can then be functionalized via an isonitrile or isocyanate intermediate through a one-pot reaction with high efficiency into a plethora of functionalities.

Example 1: This example illustrates the synthesis and polymerization of vinylbenzylformamide (VBF) monomers.

Figure 3:
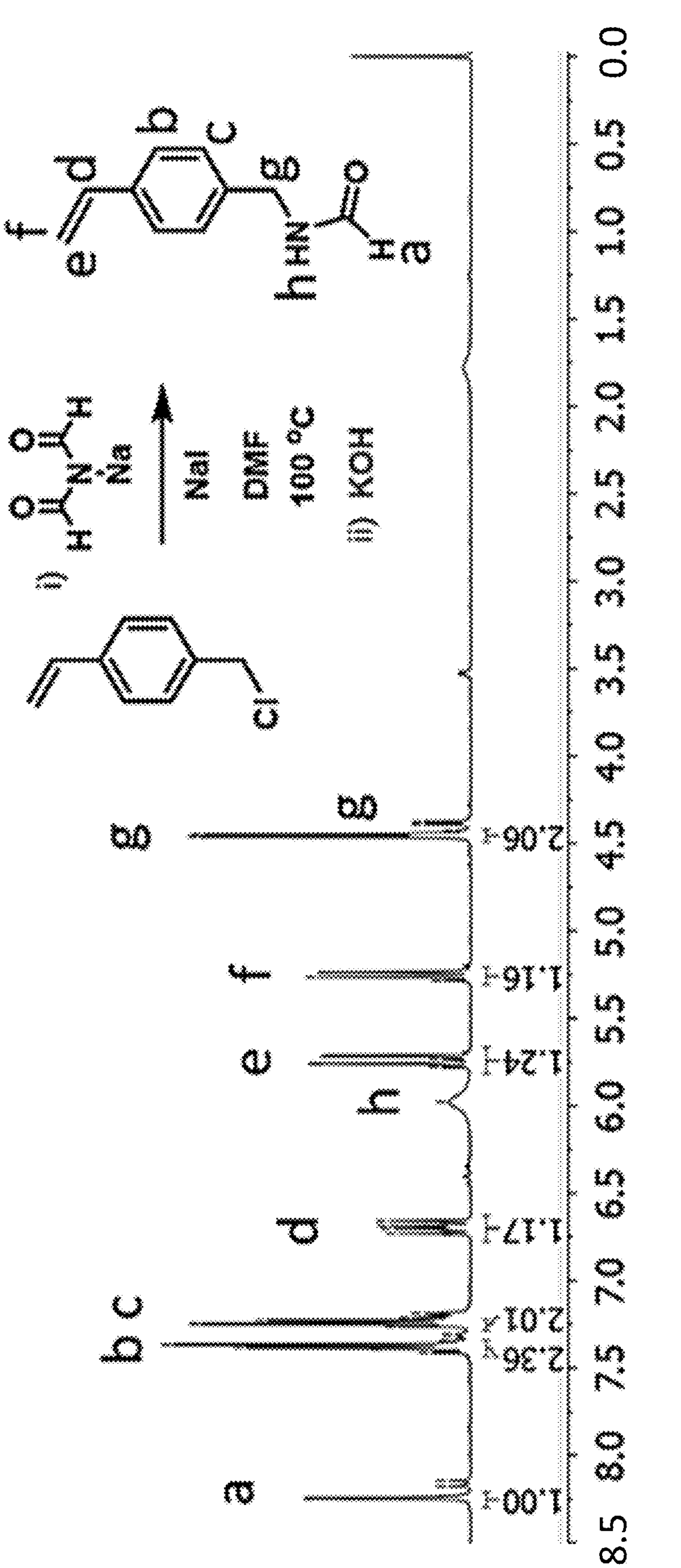
FIG. 3 depicts a synthesis scheme for a vinyl benzyl formamide (VBF) monomer and the proton nuclear magnetic resonance ($^1$H NMR) spectrum of the purified monomer.

Monomer design and synthesis: The VBF monomer was synthesized with over 75% yield. The para-substituted styrene was synthesized using the procedures described in Robertson, J. et al., *Org. Biomol. Chem.* 2005, 3 (23), 4246-4251. Starting with the commercially available vinylbenzylchloride, a one-step conversion to VBF was conducted using sodium iodide in DMF. Sodium diformylimide was added as the source of the formamide group. A typical procedure was as follows: sodium diformylimide (5.91 g, 62.24 mmol) was added to a stirred solution of vinylbenzyl chloride (5.0 g, 32.76 mmol) and sodium iodide (NaI) (10.80 g, 72.07 mmol) in DMF (40 mL), and the mixture was heated at 100° C. for 48 h. The hot reaction mixture was poured into water. The mixture was extracted with dichloromethane (DCM) (200 mL), and the combined organic phases were concentrated in vacuo. The product was further dissolved in DCM (50 mL), and KOH (0.1 g, 1.79 mmol) was added. The mixture was stirred for 1 h at room temperature, and the organic layer was concentrated in vacuo to get a pale yellow solid as the product (3.94 g, 75.5%). The product was further purified by column chromatography (silica 1:2 hexane:ethylacetate). $^{1}$H NMR confirmed the chemical structure (FIG. 3). This monomer itself is soluble in a wide range of solvents, such as DCM, chloroform, tetrahydrofuran (THF), DMF, DMSO, and methanol, and it is partially soluble in acetonitrile and hexane.

Figure 4:
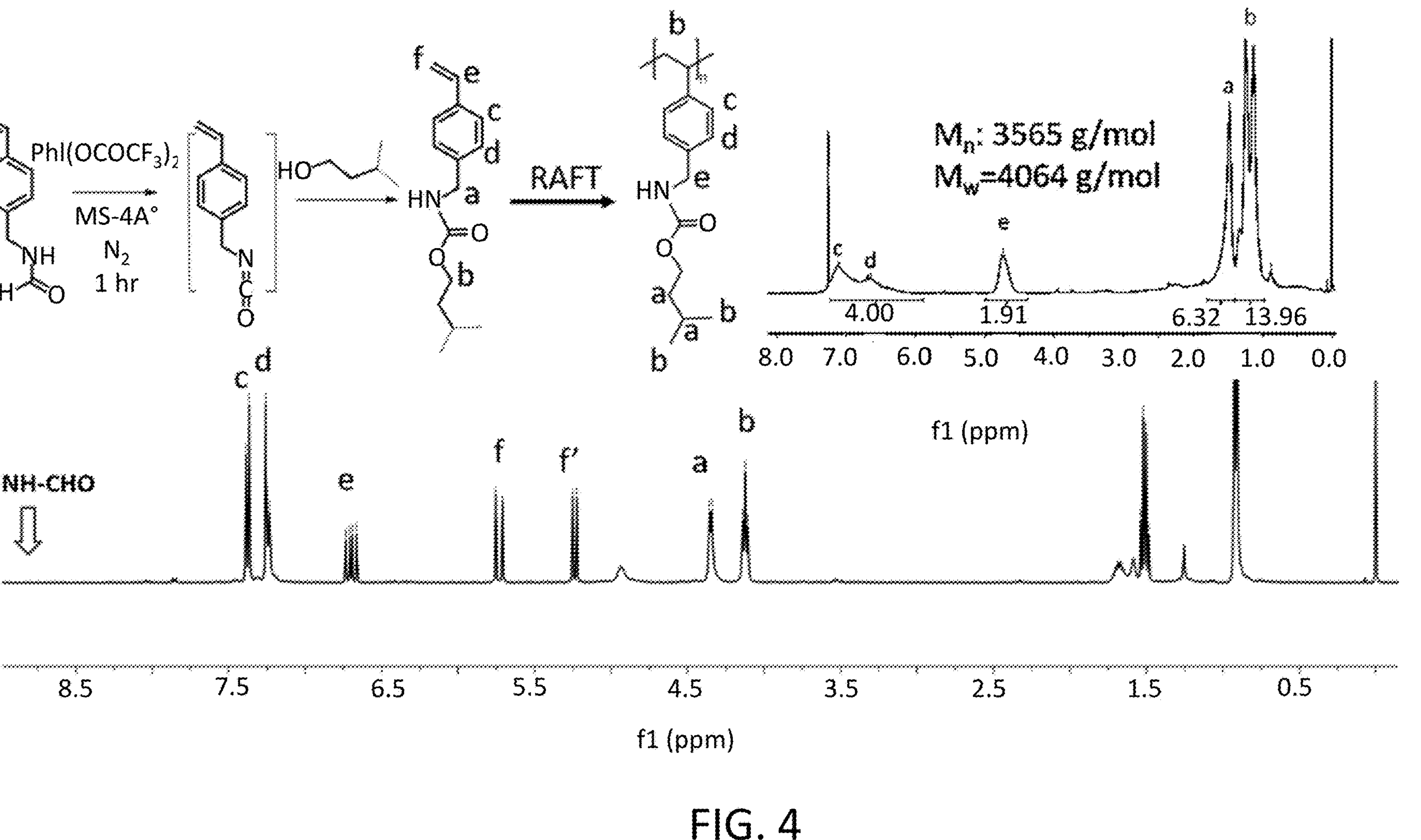
FIG. 4 depicts the conversion of the VBF monomer through one-pot chemistry to a carbamate monomer via the isocyanate intermediate, along with the $^1$H NMR spectra showing all the expected peaks and the disappearance of the CHO peak. The top inset shows the polymerization of the functionalized monomer by Reversible Addition-Fragmentation Chain Transfer (RAFT) with the resulting NMR and gas permeation chromatography (GPC) data showing a well-controlled 100% functionalized polymer.

Conversion of the formamide to carbamate link via isocyanate intermediate: To confirm the reactivity of the formamide in the VBF monomer, a simple carbamate conversion was conducted with an alcohol. 0.16 g of VBF and a pinch of MS (molecular sieve). –4A° was taken in a 50 mL round-bottomed (RB) flask with 5 mL of DCM. The reaction mixture was purged with Ar for 15 min. To this solution, 0.430 g of oxidant [$PhI(COOCF_3)_2$] in 1 mL of DCM was added, and stirring was continued for 10 min. After complete conversion of formamide to isocyanate, which was monitored by thin layer chromatography (TLC), 2-methylbutanol 0.43 g was added to the solution. The reaction was continued for 3 h. The molecular sieves were removed by filtration, and the solvent was evaporated. The crude product was purified by flash chromatography. $^{1}$H NMR confirmed complete disappearance of the formamide protons and the formation of the product through the isocyanate intermediate with quantitative yields (FIG. 4). The styrenic double bond was unaffected by this reaction and was available for polymerization. Further polymerization of this monomer by RAFT resulted in a well-defined polymer (FIG. 4, top panel).

Figures 5A, 5B:
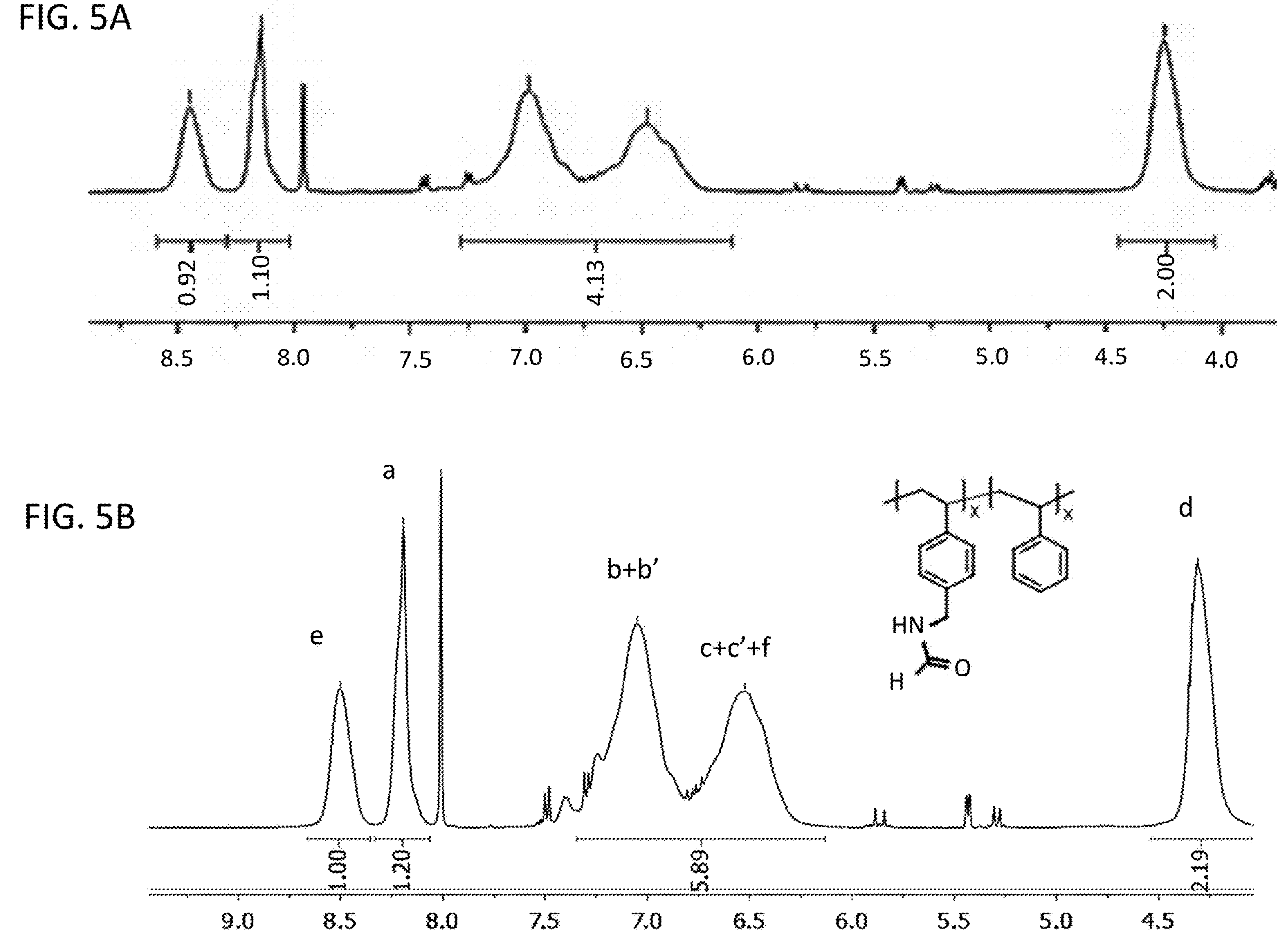
FIG. 5A depicts the $^1$H NMR spectrum of a PVBF homopolymer, along with the GPC data.
FIG. 5B shows the $^1$H NMR of a P(VBF-r-S) copolymer with a 73:27 mole ratio, along with dispersity derived from GPC.

Polymerization of VBF: The purified VBF monomer was tested for its polymerizability using multiple methods. First, conventional free radical polymerization, using azobisisobutyronitrile (AIBN) in DMF at 75° C. for 12 h, led to a polymer ($M_n$: 14.2K, Đ ($M_w/M_n$)=1.66). The feasibility of conducting controlled free radical polymerization was also explored. Of the methods available, RAFT worked the best. VBA (1.0 g, 6.2 mmol), 4-cyano-4-[(dodecylsulfanylthiocarbonyl)sulfanyl]pentanoic acid (24.9 mg, 0.05 mmol), and AIBN (2.5 mg, 0.0015 mmol) were added with 2.5 mL of DMF into a 10 mL Schlenk flask. The reaction mixture was degassed by Ar purge for 30 min, followed by three freeze-pump-thaw cycles for 15 min, then heated at 75° C. with stirring for 12 h. The reaction mixture was cooled and precipitated into a large amount of methanol. The obtained polymer was further purified by re-precipitation. The pale-yellow polymer powder was collected. Yield: 0.66 g. The structure was confirmed by $^{1}$H NMR and GPC analysis [Mn: 5.5K, $M_w/M_n$=1.14] (FIG. 5A). Hence, controlled molecular weights and dispersity can be achieved with these monomers. This polymer is soluble in methanol, DMF, and DMSO, and it is partially soluble in DCM, THF, and chloroform. VBF was also able to be copolymerized with styrene by RAFT, resulting in a polymer which was more soluble in DCM (FIG. 5B). This copolymer was further used to conduct the same carbamate conversion as in FIG. 4 via the isocyanate intermediate, resulting in over 60% conversion.

The monomer can be further homo or copolymerized by conventional and controlled free radical methods with good control over molecular weights and dispersity. Copolymerization improves the solubility in organic solvents such as DCM. It is also feasible to transform these formamide side-groups via a reactive isocyanate intermediate into carbamate linkages at the monomer and polymer stages. These results demonstrate the use of a non-toxic scalable monomer and its polymer to build a highly versatile platform for a whole range of post-functionalization reactions that are currently not available via one-pot synthesis.

Example 2 (Prophetic): This example describes various schemes for the synthesis of styrenic formamide monomers, (meth)acrylate formamide monomers, and cyclic olefin formamide monomers.

Monomers and homo- and copolymers made from the monomers can be designed to cover a wide range of solubilities in organic solvents. For example, the styrenic (VBF), (meth)acrylate, and cyclic olefin monomers shown in FIG. 6 can be synthesized. Synthetic routes are illustrated in the synthesis schemes shown in in FIG. 7A-FIG. 7G. For the styrenic monomers (FIG. 7A-FIG. 7C) the linker length (n) can be varied from 1-3 fairly easily, as the precursors (chloro, cynano, or amine) are readily available. However, the monomers can also be formed with longer linkers. For the acrylate (AF) or methacrylate (MF)-based monomers (FIG. 7D), a two-step synthesis using a commercially available ethanolamine converted to formamide derivative followed by esterification with commercially available acryloyl or methacryloyl chloride can be carried out.

Figures 7A, 7B, 7C:
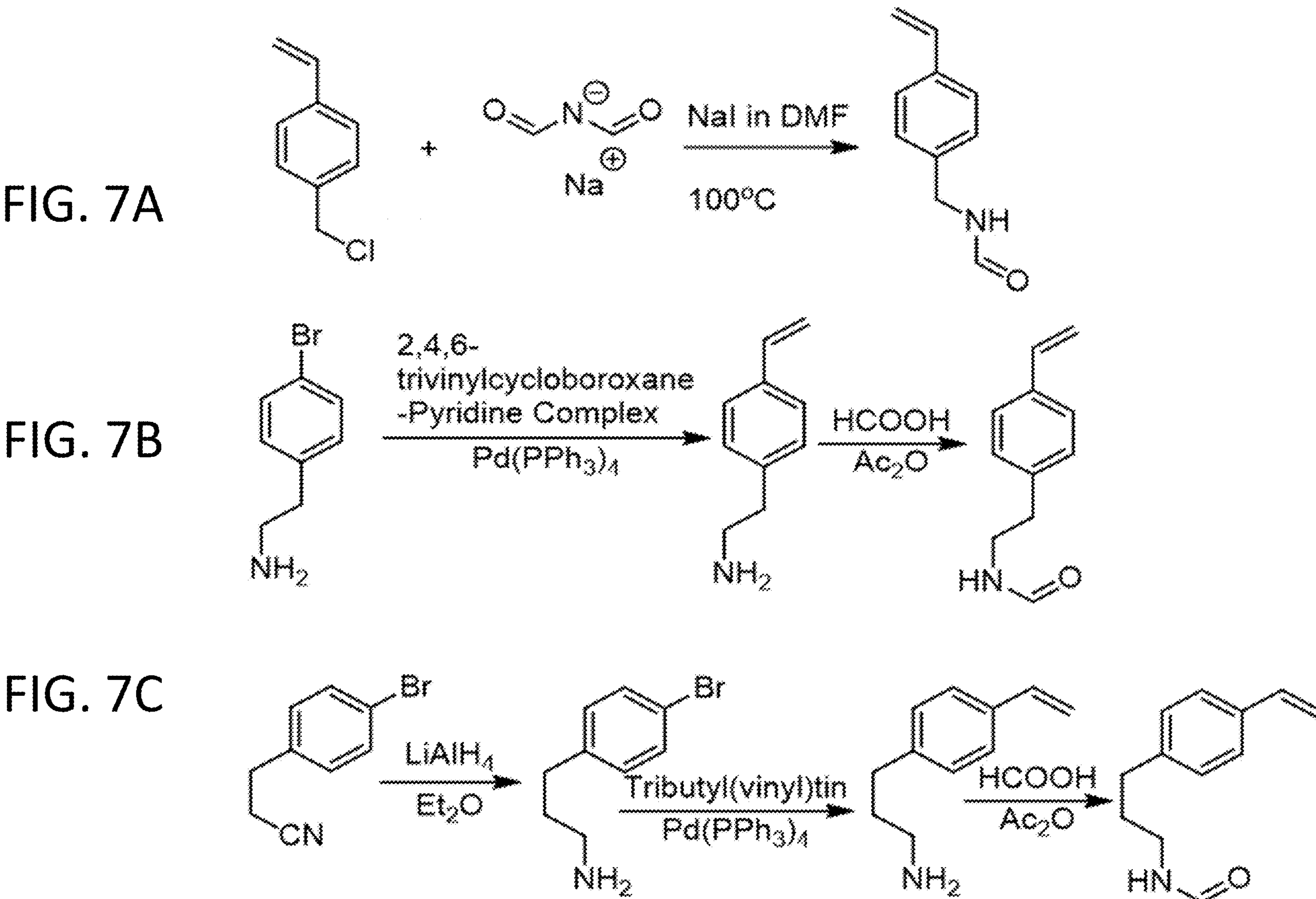
FIG. 7A-FIG. 7C depict synthetic schemes for three styrenic formamide monomers.
Figure 7D:
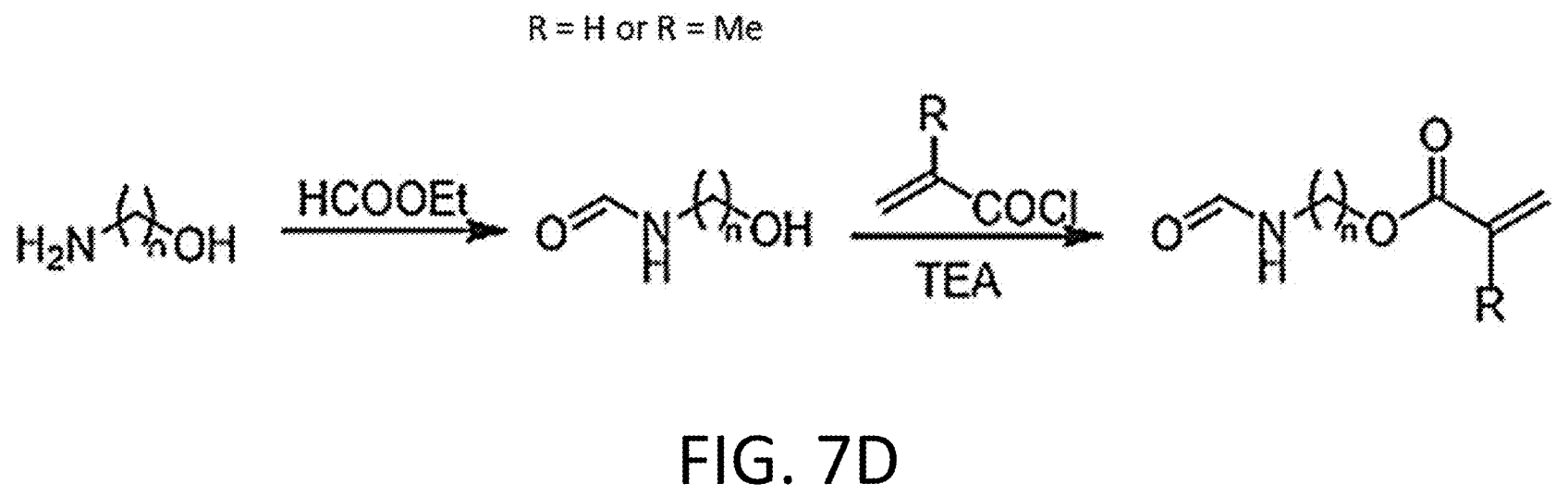
Figures 7E, 7F, 7G:
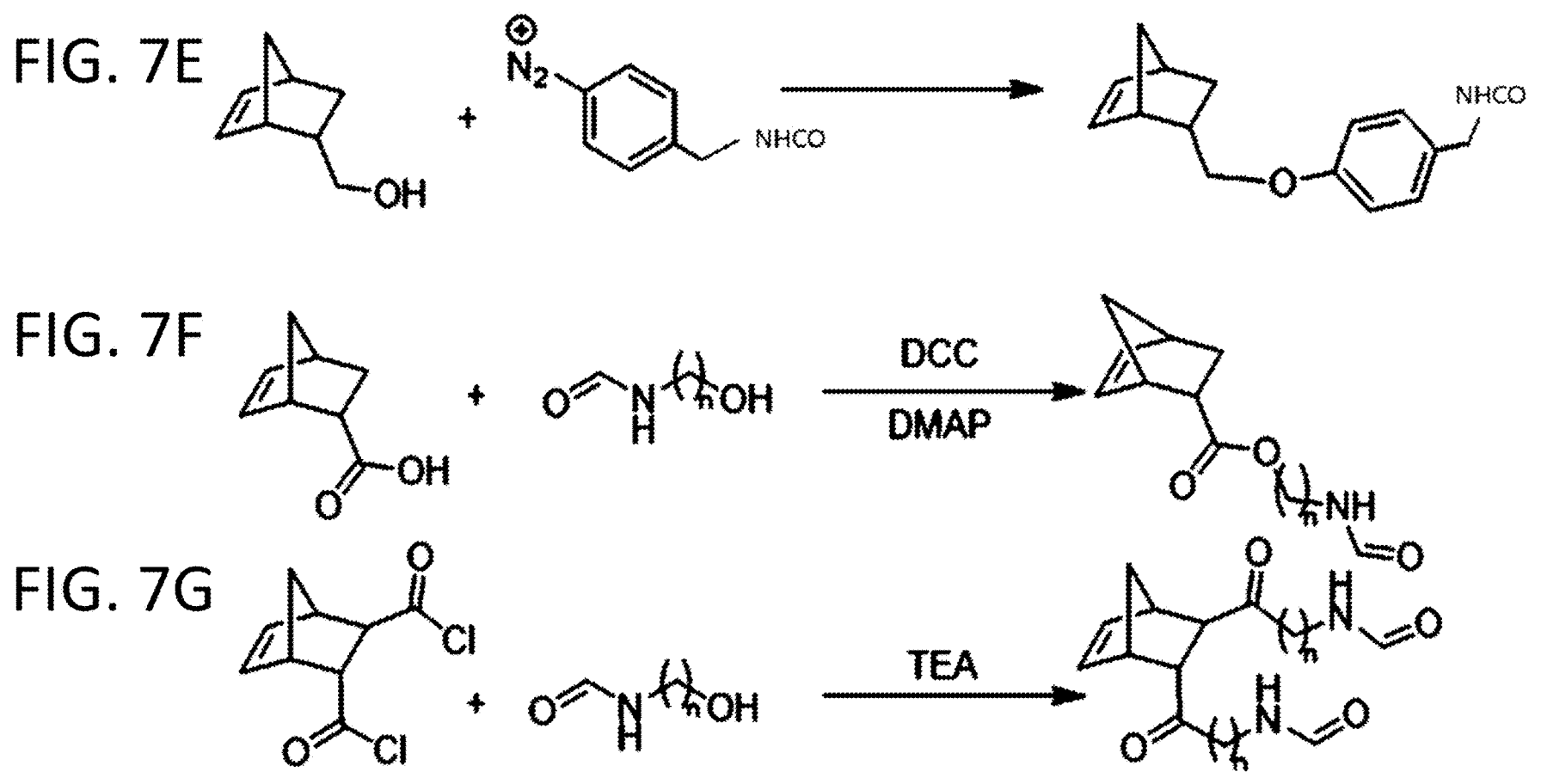
Figure 7H:
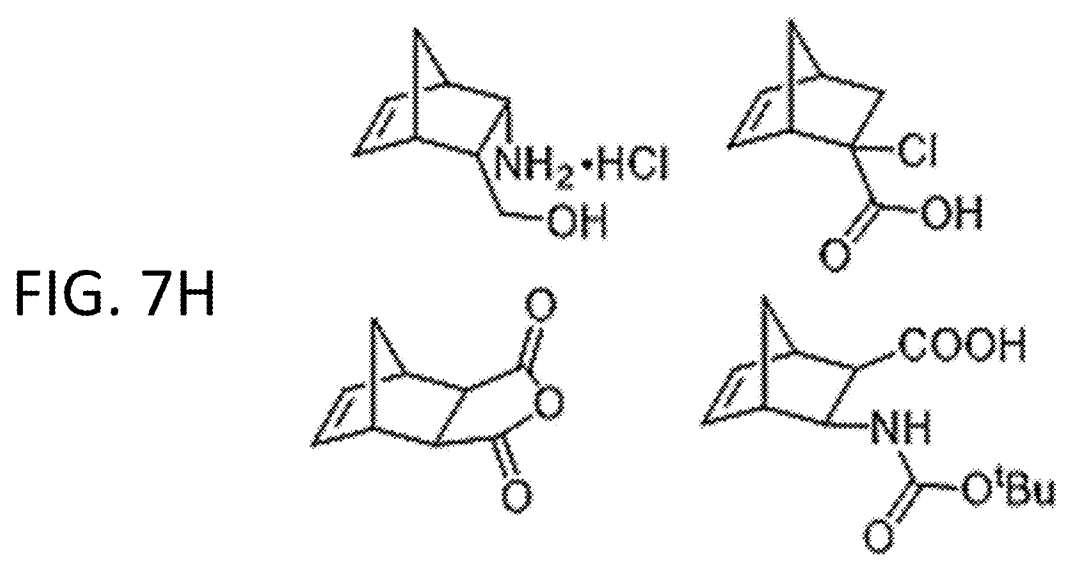

In the case of cyclic olefin monomers, both aryl formamide (FIG. 7E) and alkyl-formamide functionalized norbornene monomers (FIG. 7F, FIG. 7G) can be synthesized. A proposed synthesis of these monomers is outlined in FIG. 7A-FIG. 7G. With the ROMP monomers, the bifunctional monomer can also be made, giving added functionality to the polymer. Alternative norbornene derivatives that can be used the synthesis of the ROMP monomers are shown in FIG. 7H.

Example 3 (Prophetic): This example describes various polymerization schemes for formamide monomers.

The formamide monomers are a versatile platform, as they can be exploited using two approaches to create functionalized polymers. The first approach is to convert the monomers through an isocyanate/isonitrile intermediate to a new functionalized monomer and then polymerize the functionalized monomers (FIG. 8) to form a polymer. The second approach is to polymerize the formamide monomer itself and then functionalize the polymer. The first approach is essentially small molecule chemistry, which can be nearly quantitative. The subsequent polymerization of the functionalized monomers can proceed by RAFT, ATRP, or ROMP. This approach also allows mixing of various functionalized monomers in a predetermined feed ratio to synthesize copolymers with chosen compositions. The first approach is a multi-step process that may require synthesis and purification of the functionalized monomers before polymerization. The second approach is more user friendly and can provide a blank slate which can be used for further functionalization at the user end. This blank slate can be used for solid supports, microcarriers, etc. for further functionalization. Together, these approaches, which are described in more detail below, highlight the versatility of this platform and provide guidance for a massive expansion of the functional tool-kit available to polymer chemists.

Figure 2:
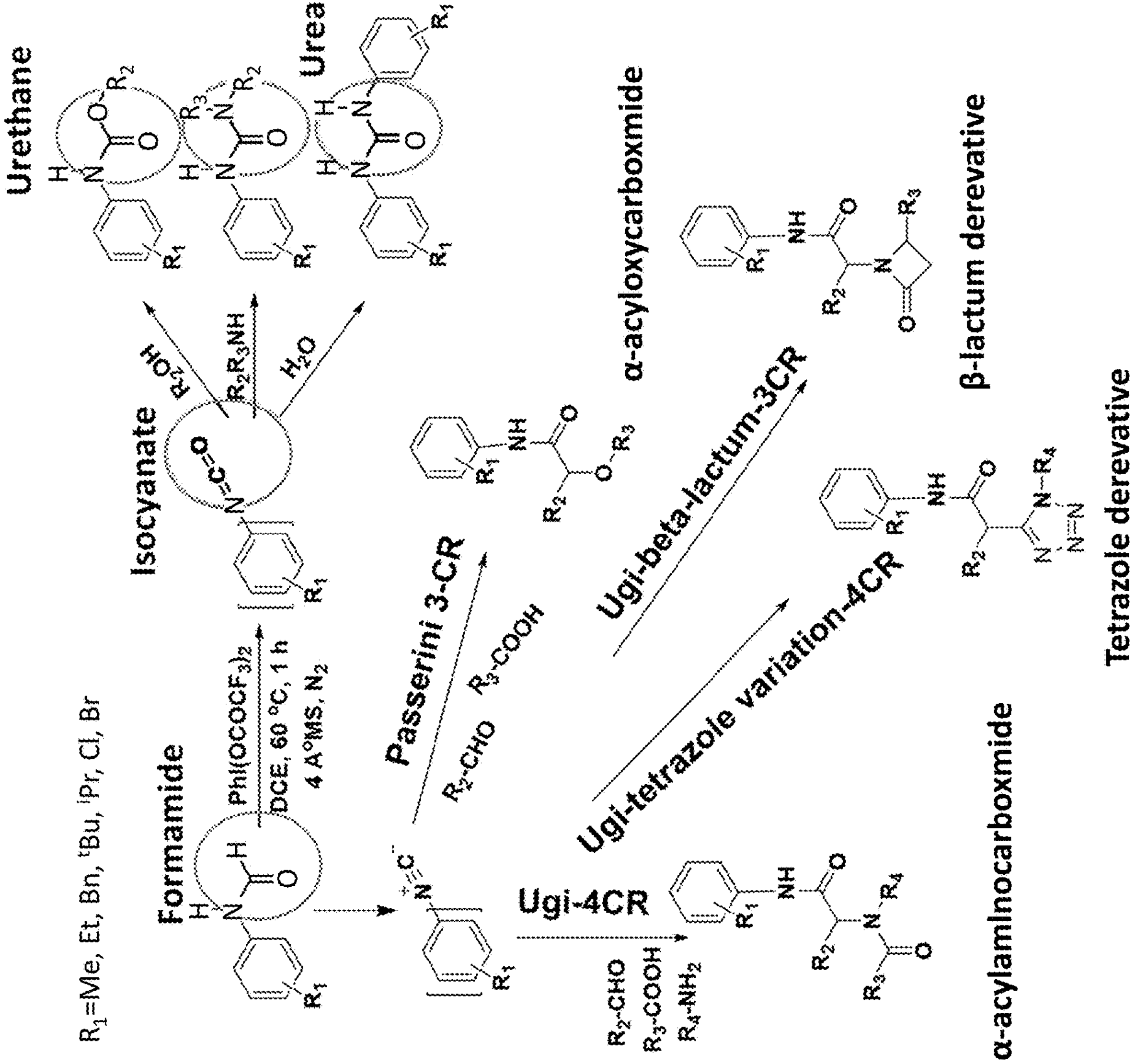
FIG. 2 depicts small molecule transformations of formamide to isocyanate and isocyanide intermediates and their subsequent functionalization to urea, urethane, and acyloxycarboxamide and acylaminocarboxamide derivatives using one-pot MCR. These transformations can be applied to the formamide-functionalized polymers described herein.
Figure 8:
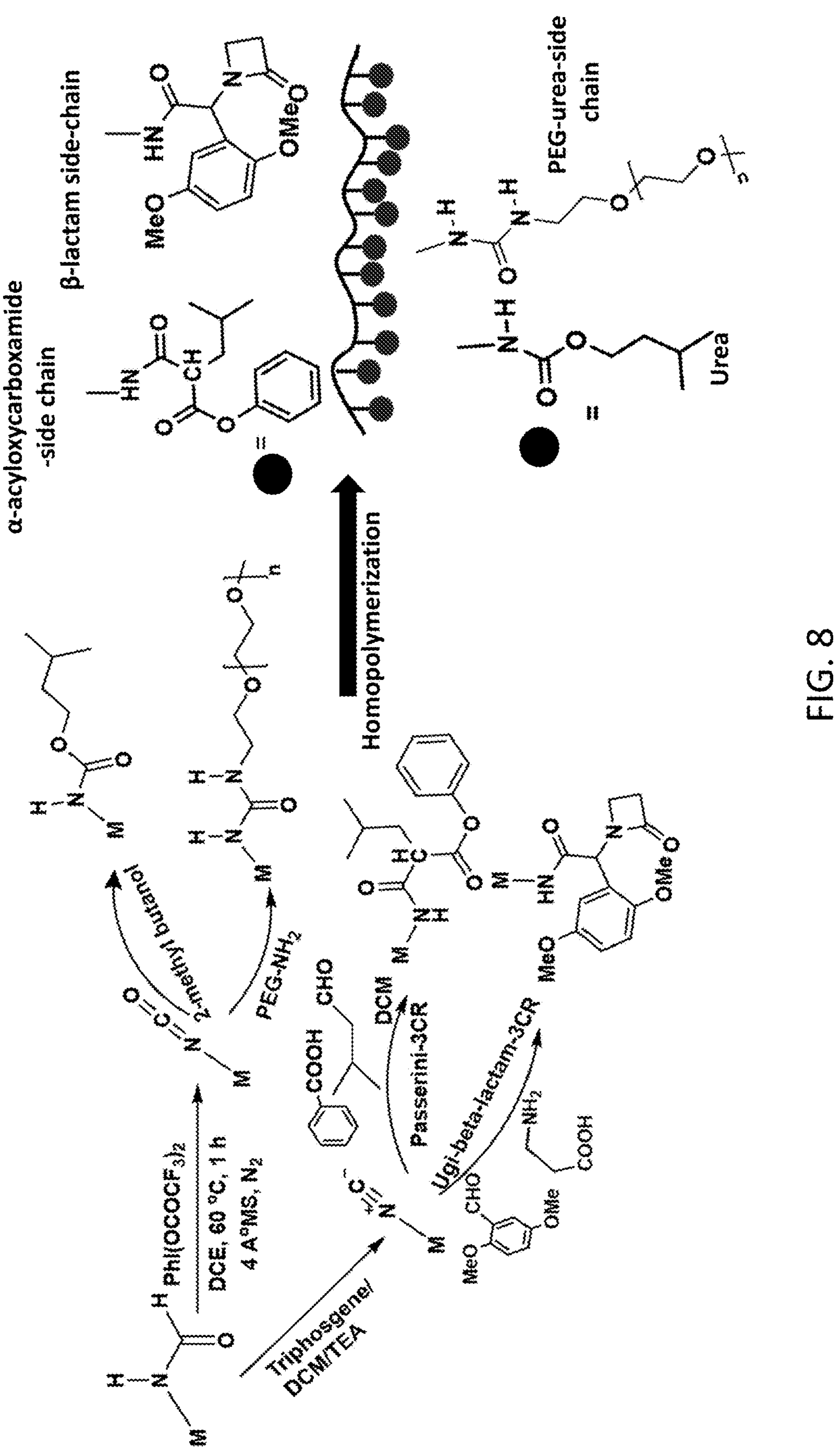
FIG. 8 depicts four reactions for the formation of urea, urethane, acyloxycarboxamide, and β-lactam side-chain functionalized monomers. M stands for any of the monomers based on VBF, (M)AF, or NBF. The right side shows the resulting side-chain functionalized homopolymers (Approach 1).

Approach 1: Polymerization of functionalized monomers: A subset of transformations that illustrate the polymerization and the pre- and post-polymerization functionalization of formamide monomers are described here. These transformations include conversion of the formamide monomer to: (a) a carbamate monomer with a simple alcohol (2-methyl butanol) via the isocyanate intermediate, (b) a urea monomer with an oligomeric primary amine [Aminopolyethylene glycol monomethyl ether (PEG-$NH_2$), 2000 g/mol from sigma Aldrich] via the isocyanate intermediate, (c) the acyloxy-carboxamide monomer by reaction with an aldehyde (2-methyl butaraldehyde) and acid (benzoic acid) using the Passerini-3CR via the isonitrile intermediate, and (d) the β-lactam monomer using the Ugi-β-lactam-3CR via the isonitrile intermediate by reacting with an aldehyde (2,5-dimethoxybenzaldehyde) and an amino acid (β-Alanine). Reaction schemes that can be used for these conversions are shown in FIG. 2 and FIG. 8. These transformations result in important linkages in polymer chemistry for conjugation of a wide range of oligomers, small molecules, and peptides. The side-chain PEG functionalized polymers resulting from transformation (b) above are an important class of polymers for biomaterials, coatings, and other responsive surfaces. The β-lactam functionality from the Ugi-lactam reaction is incredibly interesting and valuable for generating Nylon-3 polymers. These Nylon-3 polymers are similar to proteins and peptides derived from α-amino acids; hence, they have been explored for a range of biological properties including toxicity to bacteria, and cell growth and expansion. Having a β-lactam functionality in the side chain can generate different architectures, such as comb or bottle-brush copolymers.

Synthesis of double headed inimers and bottle-brush copolymers: To demonstrate functional polymer architectures, the following description is provided, where multi-component reactions are used to synthesize a double-headed orthogonal initiator, which is also a monomer. The combination of monomer and initiator is referred to as "inimer." These inimers include an ATRP initiator and an NMP initiator in a Y-shaped architecture attached to the formamide monomer. When polymerized, the proposed Y-shaped inimer will have both these initiating sites on each repeat unit.

Figure 9:
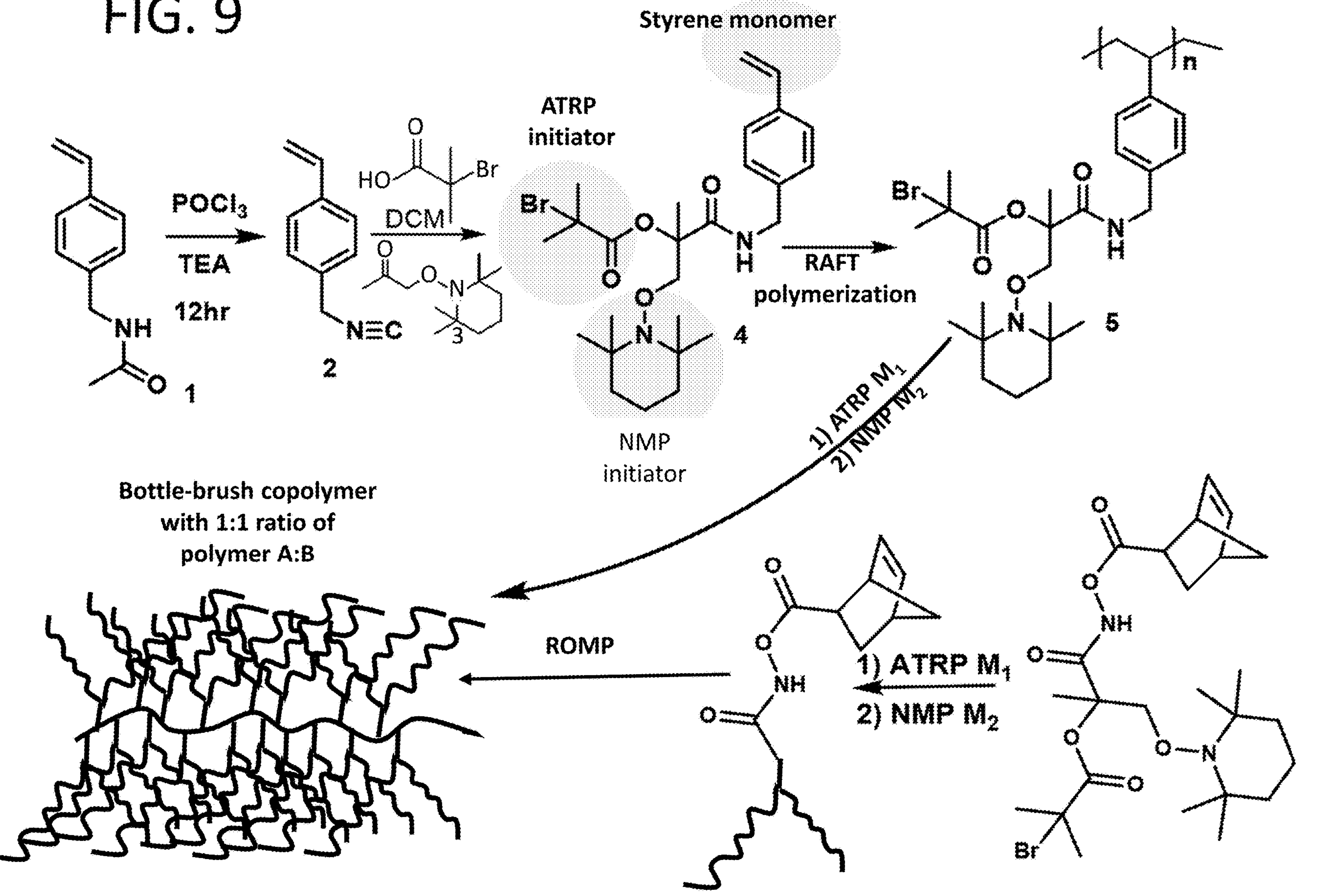
FIG. 9 depicts a scheme for implementing a 3-CR Passerini reaction on a formamide monomer to synthesize a Y-shaped inimer. The Y-shaped inimer can be polymerized and the polymer used to synthesize bottle-brush copolymers using orthogonal polymerization mechanisms (nitroxide mediated radical, NMP and atom transfer radical polymerization, ATRP). ROMP inimers can be first used to grow polymer A and B and then the monomers can be polymerized. Alternatively, the formamide monomers can be polymerized prior to brush growth.

This type of architecture is incredibly useful for synthesizing bottle-brush copolymers. Bottle-brush copolymers themselves are a class of comb polymers in which the backbone is longer than the side chains. In this architecture, the steric repulsion between the side chains leads to an extended chain conformation of the backbone. As a result, high aspect ratio cylindrical bottle brushes can be synthesized. The Y-shaped inimer can result in a bottle-brush copolymer with 1:1 ratio of Polymer A and Polymer B "grafted from" the monomer using orthogonal chemistry. The choices of Polymer A and Polymer B grafted to the backbone are vast, only limited by the polymerization method, namely NMP or ATRP. This approach can be applied to the entire set of monomers in FIG. 6. One such example, based on VBF monomer, is presented in FIG. 9. The NBF monomers (FIG. 9, bottom panel) are particularly effective due to the efficiency of the ROMP method even in sterically hindered monomers. The aromatic VBF and NBF monomers can be used to form a 1:1 bottle-brush copolymer with polystyrene (PS) and polymethylmethacrylate (PMMA) as Polymer A and B, respectively.

Figure 10:
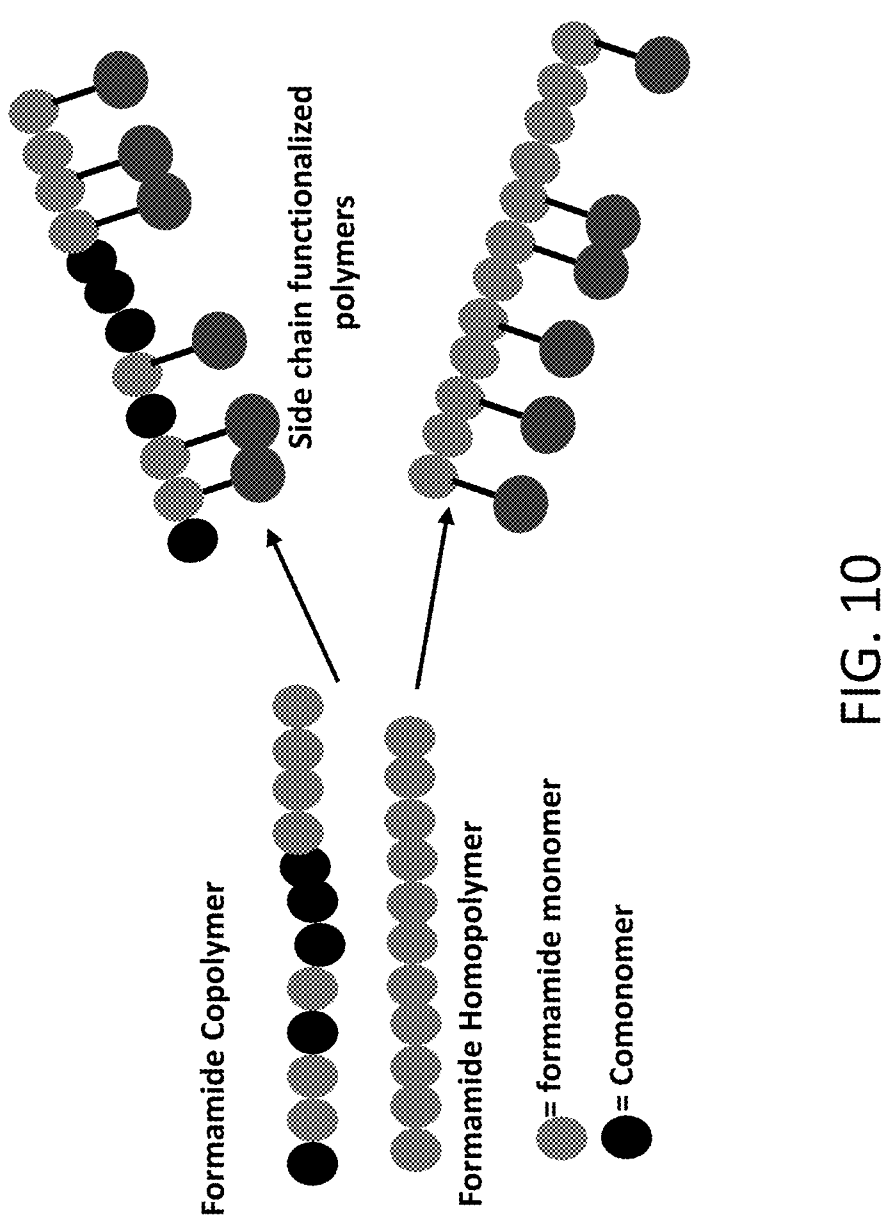
FIG. 10 depicts a schematic representation of homo and copolymers of formamide monomers and their subsequent transformation to functionalized polymers.
Figure 11:
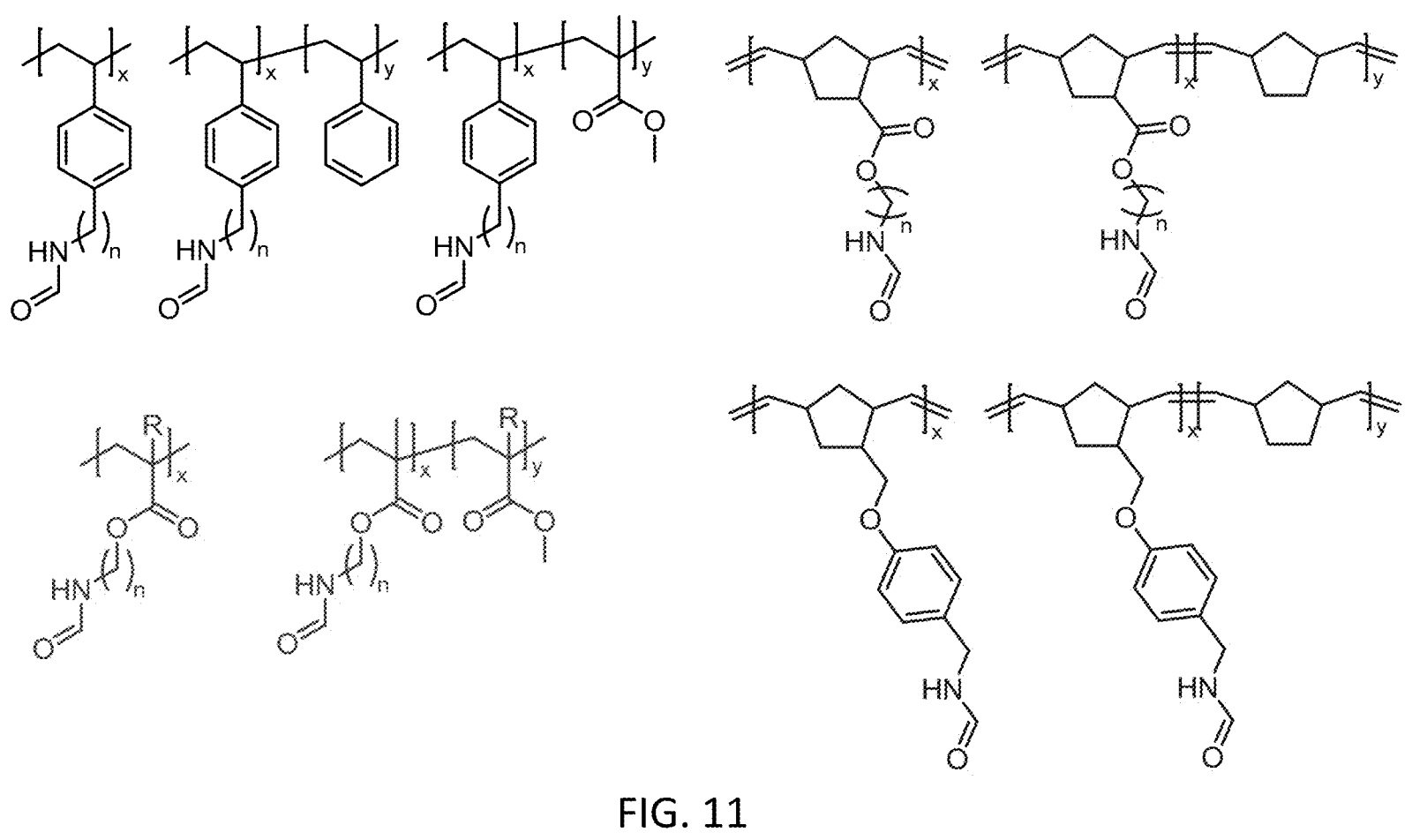

Approach 2: Polymerization and co-polymerization of formamide monomers: All the proposed styrenic and (meth) acrylate monomers are first homopolymerized by RAFT or ATRP. These two methods offer sufficient choices in the solvent, ligand, temperature, and catalyst systems to ensure that the conditions for polymerization can be optimized (FIG. 10). FIG. 11 shows the structures of the polymers made from the monomers of FIG. 6. For the cyclic olefin monomers, efficient polymerization may be achieved using the standard Grubbs (G3) ruthenium catalyst, as it is known for excellent functional group tolerance, fast initiation and propagation, and for essentially being a living polymerization. Typically, solvents such as DCM work quite well for ROMP at room temperatures. To further tune the solubility of the resulting polymers, a series of copolymers with 30, 50, and 80 mole percent of the formamide monomer can be synthesized with the MMA or NB monomer. Preliminary studies indicate that the VBF monomer copolymerization with MMA (data not shown) improves the solubility in DCM more than copolymerization with styrene. Hence, copolymers of MMA monomers and VBF, AF, and/or MF monomers can be made. The formamide monomers can be used to form block copolymers (BCPs). One BCP with a 1:1 volume ratio of formamide monomer can be synthesized with a second monomer, namely PVBF-b-PMMA, PNBF-b-PNB, and PMAF-b-PMMA.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of forming a functionalized polymer from a polymer having pendant formamide groups, the method comprising:

providing monomers having polymerizable groups, wherein at least some of the monomers have the polymerizable group and a formamide group;

reacting the polymerizable groups of the monomers to form a polymer, wherein the polymerizable groups form a polymer backbone and the formamide groups are pendant from the polymer backbone; and reacting the polymer with one or more additional components in a one-pot multicomponent reaction, whereby at least some of the pendant formamide groups are converted into isocyanate groups or isonitrile groups and at least some of said isocyanate groups or isonitrile groups are transformed into different functional groups during the one-pot multicomponent reaction.

2. The method of claim 1, wherein the one-pot multicomponent reaction uses two or more additional components.

3. The method of claim 1, wherein at least some of the formamide pendant groups are converted into the isocyanate groups.

4. The method of claim 2, wherein the one or more additional components comprise a primary amine.

5. The method of claim 3, wherein at least some of the isocyanate groups are transformed into carbamate groups.

6. The method of claim 5, wherein the one or more additional components comprise an alcohol.

7. The method of claim 3, wherein at least some of the isocyanate groups are transformed into carbamide groups.

8. The method of claim 7, wherein the one or more additional components comprise a primary amine.

9. The method of claim 1, wherein at least some of the formamide pendant groups are converted into isonitrile groups.

10. The method of claim 9, wherein the one or more additional components comprise an aldehyde and an acid.

11. The method of claim 9, wherein at least some of the isonitrile groups are transformed into B-lactam groups.

12. The method of claim 11, wherein the one or more additional components comprise an aldehyde and an amino acid.

13. The method of claim 9, wherein at least some of the isonitrile groups are transformed into acylaminocarboxamide groups.

14. The method of claim 13, wherein the one or more additional components comprise an aldehyde, an acid, and a primary amine.

15. The method of claim 9, wherein at least some of the isonitrile groups are transformed into tetrazole groups.

16. The method of claim 15, wherein the one or more additional components comprise an aldehyde, a primary amine, and ammonia.

17. The method of claim 16, wherein at least some of the formamide pendant groups are ATRP initiating groups, NMP initiating groups, or a combination thereof.

18. A method of forming a functionalized polymer from monomers having polymerizable groups, at least some of the monomers having the polymerizable group and a formamide group, the method comprising:

reacting the formamide groups of the monomers with one or more additional components in a one-pot multicomponent reaction, whereby at least some of the formamide groups are converted into isocyanate groups or isonitrile groups and at least some of said isocyanate groups or isonitrile groups are transformed into different functional groups during the one-pot multicomponent reaction; and subsequently reacting the polymerizable groups of the monomers to form the functionalized polymer.

19. The method of claim 18, wherein the one-pot multicomponent reaction uses two or more additional components.

20. The method of claim 18, wherein the one or more additional components comprise: a primary amine; an aldehyde and an acid; an aldehyde and an amino acid; an aldehyde, an acid, and a primary amine; or an aldehyde, a primary amine, and ammonia.

21. The method of claim 3, wherein at least some of said isocyanate groups are transformed into urethane groups or urea groups.

22. The method of claim 10, wherein at least some of the isonitrile groups are transformed into acyloxycarboxamide groups.

23. The method of claim 1, wherein the polymerizable groups comprise vinyl groups and the monomers are vinyl aromatic monomers.

24. The method of claim 1, wherein the polymerizable groups comprise acrylate groups or methacrylate groups.

25. The method of claim 1, wherein the polymerizable groups comprise cyclic olefin groups.

26. The method of claim 18, wherein the polymerizable groups comprise vinyl groups and the monomers are vinyl aromatic monomers.

27. The method of claim 18, wherein the polymerizable groups comprise acrylate groups or methacrylate groups.

28. The method of claim 18, wherein the polymerizable groups comprise cyclic olefin groups.

* * * * *